(12) United States Patent
Goshima et al.

(10) Patent No.: US 12,269,949 B2
(45) Date of Patent: Apr. 8, 2025

(54) POLYIMIDE COMPOUND AND MOLDED ARTICLE COMPRISING THE POLYIMIDE COMPOUND

(71) Applicant: WINGO TECHNOLOGY CO., LTD., Okayama (JP)

(72) Inventors: Toshiyuki Goshima, Okayama (JP); Win Maw Soe, Okayama (JP)

(73) Assignee: WINGO TECHNOLOGY CO., LTD., Okayama (JP)

(*) Notice: Subject to any disclaimer, the term of this patent is extended or adjusted under 35 U.S.C. 154(b) by 769 days.

(21) Appl. No.: 17/427,670

(22) PCT Filed: Feb. 1, 2019

(86) PCT No.: PCT/JP2019/003595
§ 371 (c)(1),
(2) Date: Aug. 2, 2021

(87) PCT Pub. No.: WO2020/157953
PCT Pub. Date: Aug. 6, 2020

(65) Prior Publication Data
US 2022/0162445 A1 May 26, 2022

(51) Int. Cl.
*C08L 79/08* (2006.01)
*C08G 73/10* (2006.01)

(52) U.S. Cl.
CPC .......... *C08L 79/08* (2013.01); *C08G 73/1032* (2013.01); *C08G 73/1039* (2013.01); *C08G 73/1042* (2013.01); *C08G 73/1046* (2013.01); *C08G 73/1078* (2013.01); *C08L 2201/08* (2013.01); *C08L 2201/10* (2013.01); *C08L 2203/20* (2013.01); *C08L 2203/30* (2013.01)

(58) Field of Classification Search
None
See application file for complete search history.

(56) References Cited

U.S. PATENT DOCUMENTS

| | | | |
|---|---|---|---|
| 2012/0015298 A1* | 1/2012 | Takao | G03F 7/037 430/283.1 |
| 2015/0241739 A1 | 8/2015 | Park et al. | |
| 2015/0307662 A1 | 10/2015 | Oka et al. | |
| 2017/0059755 A1 | 3/2017 | Yoo et al. | |
| 2018/0284543 A1* | 10/2018 | Mandai | C09K 19/56 |
| 2021/0171714 A1* | 6/2021 | Miura | C08G 73/126 |

FOREIGN PATENT DOCUMENTS

| | | |
|---|---|---|
| CN | 103608382 A | 2/2014 |
| CN | 105829400 A | 8/2016 |
| JP | 2007112990 A | 5/2007 |
| JP | 2012068612 A | 4/2012 |
| JP | 6240798 B1 * | 11/2017 |
| JP | 6240799 B1 * | 11/2017 |
| JP | 2018118947 A | 8/2018 |
| KR | 20180099863 A | 9/2018 |
| TW | 201833074 A | 9/2018 |
| WO | WO-2015083649 | 6/2015 |
| WO | WO-2017051827 A1 | 3/2017 |
| WO | WO-2017057496 | 4/2017 |
| WO | WO-2018139311 | 8/2018 |

OTHER PUBLICATIONS

English language machine translation of JP 6240799 (Year: 2017).*
English language machine translation of JP 6240798 (Year: 2017).*
Combined Chinese Office Action and Search Report issued Aug. 24, 2022 in Patent Application No. 201980000492.5 (with English translation).
English translation of the International Preliminary Report on Patentability and Written Opinion issued Aug. 12, 2021 in PCT/JP2019/003595, 7 pages.
Combined Taiwanese Office Action and Search Report issued Nov. 21, 2019 in Patent Application No. 108105768 (with English translation), 8 pages.
International Search Report issued Apr. 16, 2019 in PCT/JP2019/003595, 2 pages.
Office Action issued Apr. 29, 2020 in Korean Patent Application No. 10-2019-7009060 (with English translation), 16 pages.
Office Action issued Jan. 17, 2020 in Japanese Patent Application No. 2019-510990 (with English translation), 5 pages.

(Continued)

Primary Examiner — Megan McCulley
(74) Attorney, Agent, or Firm — Element IP, PLC

(57) ABSTRACT

Provided a polyimide compound having high heat resistance and transparency. The polyimide compound according to the present invention is characterized in that it is a reaction product of a diamine compound represented by the following general formula (1):

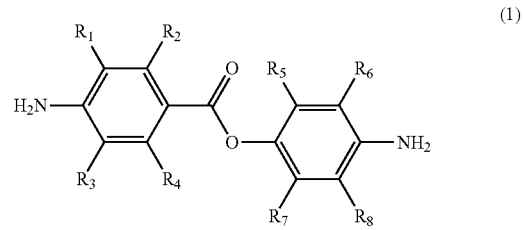

and an alicyclic tetracarboxylic acid dianhydride represented by the following general formula (2).

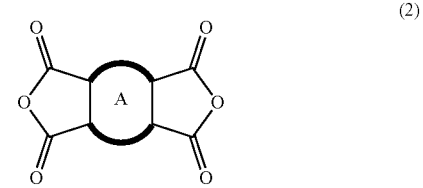

14 Claims, 2 Drawing Sheets

(56) References Cited

OTHER PUBLICATIONS

Office Action issued in Nov. 8, 2019 in Japanese Patent Application No. 2019-510990 (with English translation), 5 pages.
Extended European Search Report issued Sep. 9, 2022 in Patent Application No. 19914003.9, 8 pages.

* cited by examiner

3405cm⁻¹, 3332cm⁻¹: amine N-H expansion and contraction
3056cm⁻¹, 3037cm⁻¹: aromatic C-H expansion and contraction
1706cm⁻¹: ester C=O expansion and contraction
1595cm⁻¹: amine N-H deformation
1620cm⁻¹, 1512cm⁻¹: aromatic C=C expansion and contraction
1310cm⁻¹: amine C-N expansion and contraction
1273cm⁻¹: ester antisymmetric C-O-C expansion and contraction

POLYIMIDE COMPOUND AND MOLDED ARTICLE COMPRISING THE POLYIMIDE COMPOUND

BACKGROUND OF THE INVENTION

Field of the Invention

The present invention relates to a polyimide compound and a molded article containing the same.

Background Art

In general, polyimide compounds have excellent mechanical strength, wear resistance, dimensional stability, chemical resistance, and insulating properties in addition to high heat resistance, and are applied in various fields.

For example, in recent years, their application to optical purposes and display purposes has been in progress, and polyimide compounds applied in such fields are required to have high transparency.

The present inventors have proposed in the previous application (Japanese Patent Application No. 2017-013567) a diamine compound having a specific structure.

SUMMARY OF THE INVENTION

Problems to be Solved by the Invention

The present inventors have now found that a polyimide compound which is a reaction product of a diamine compound proposed in the previous application and an acid anhydride having a specific structure, has remarkably improved high heat resistance and transparency.

Accordingly, the problem of the present invention is to provide a polyimide compound having high heat resistance and transparency.

It is also a problem of the present invention to provide a molded article containing the polyimide compound.

Means for Solving the Problem

The polyimide compound according to the present invention is characterized in that it is a reaction product of a diamine compound represented by the following general formula (1):

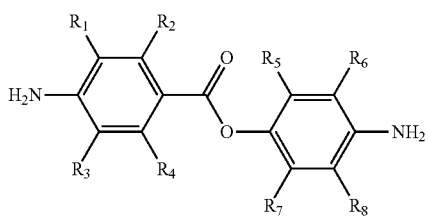

wherein
$R_1$ to $R_8$ are each independently selected from the group consisting of hydrogen, fluorine, substituted or unsubstituted alkyl groups and substituted or unsubstituted aromatic groups, and at least one of $R_1$ to $R_8$ is a substituted or unsubstituted aromatic group,
and an alicyclic tetracarboxylic acid dianhydride represented by the following general formula (2):

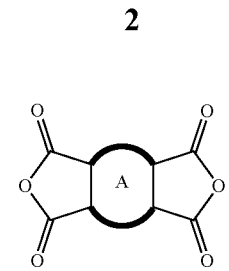

wherein
A represents an alicyclic structure.

In one embodiment, A in the above general formula (2) has the following structure.

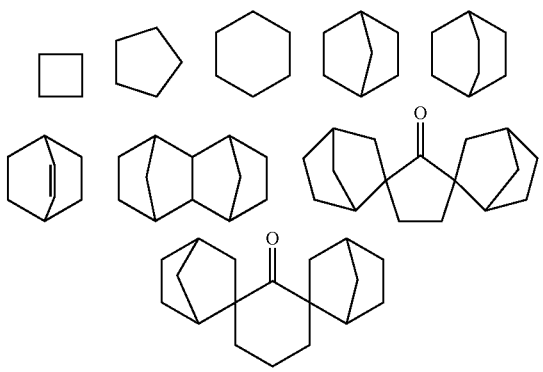

In one embodiment, the content of the diamine compound represented by general formula (1) in the polyimide compound is 5 mol % to 50 mol %.

In one embodiment, the content of the alicyclic tetracarboxylic acid dianhydride represented by general formula (2) in the polyimide compound is 10 mol % to 60 mol %.

In one embodiment, one or two of $R_5$ to $R_8$ are substituted or unsubstituted aromatic groups.

In one embodiment, one or two of $R_5$ to $R_8$ are substituted or unsubstituted aromatic groups, and $R_1$ to $R_8$ other than aromatic groups are selected from the group consisting of hydrogen, fluorine and substituted or unsubstituted alkyl groups.

In one embodiment, the substituted or unsubstituted aromatic group is selected from the group consisting of phenyl, methylphenyl, phenoxy, benzyl and benzyloxy groups.

In one embodiment, the polyimide compound of the invention further comprises a fluorene compound as a polymerization component.

In one embodiment, the fluorene compound is selected from the following compounds:

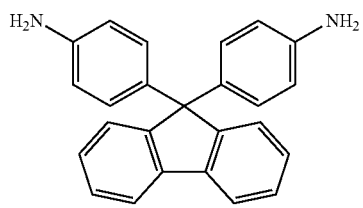

-continued

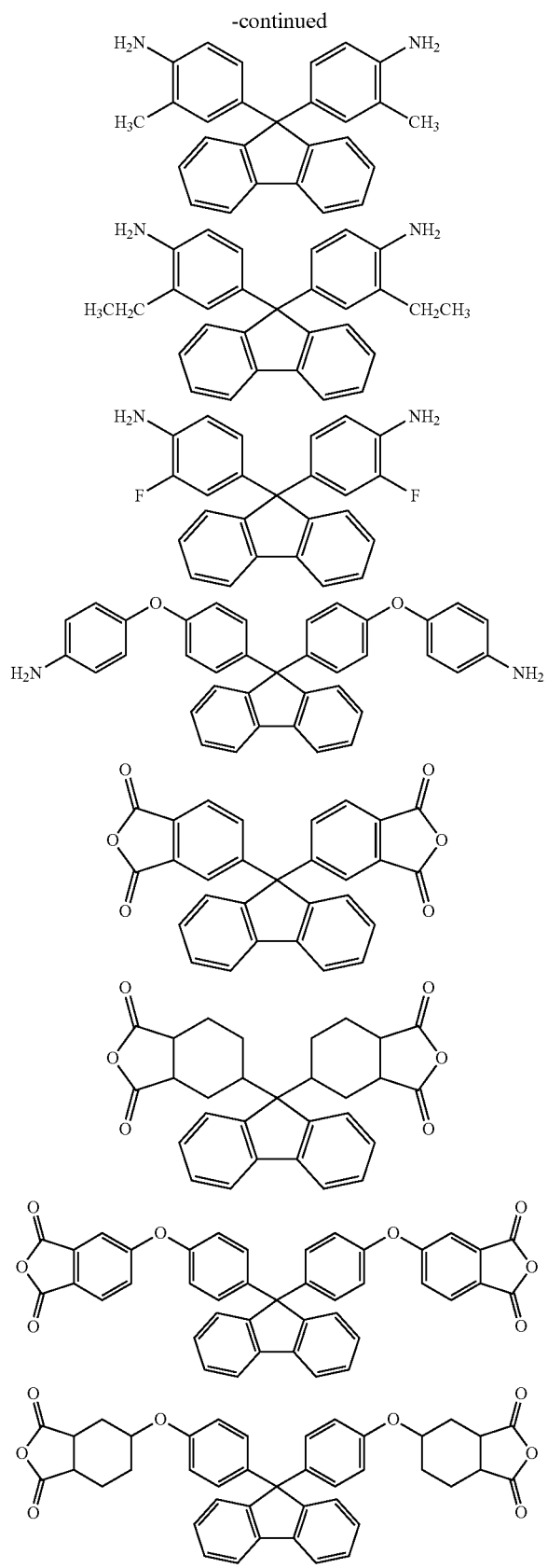

In one embodiment, the content of the fluorene compound in the polyimide compound is 5 mol % to 60 mol %.

The molded article of the present invention is characterized in that it comprises the above-described polyimide compound.

In one embodiment, the molded article has a total light transmittance of 85% or more.

In one embodiment, the molded article has a coefficient of thermal expansion (CTE) of 35 ppm/K or less.

In one embodiment, a molded article has a 5% weight loss temperature of 420° C. or higher.

In one embodiment, a molded article has a glass transition temperature of 280° C. or higher.

Effects of the Invention

According to the present invention, a polyimide compound having high heat resistance and transparency can be provided.

Further, according to the present invention, a molded article containing the polyimide compound can be provided.

Figure 1:
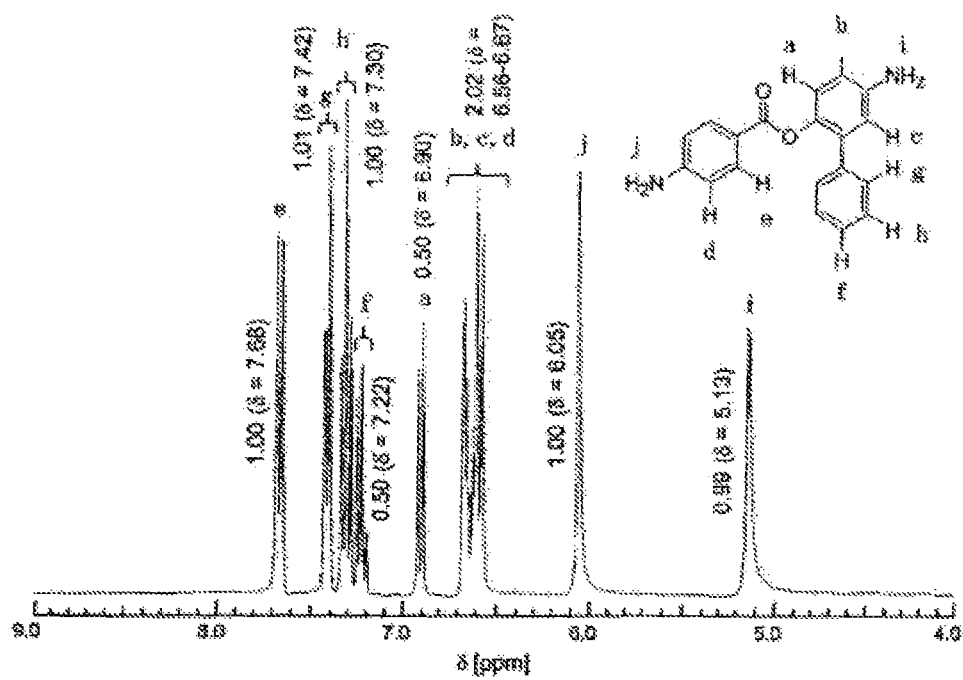
FIG. 1 shows a $^1$H-NMR chart of a compound represented by formula (D) obtained according to the Examples.

MODE FOR CARRYING OUT THE INVENTION (Polyimide Compound)

The polyimide compound according to the present invention is characterized in that it is a reaction product of a diamine compound represented by the following general formula (1):

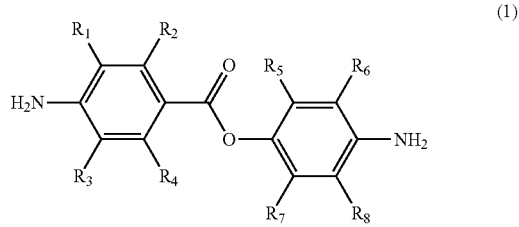

and an alicyclic tetracarboxylic acid dianhydride represented by the following general formula (2).

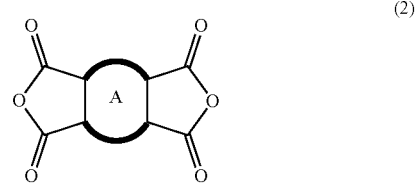

The number average molecular weight of the polyimide compound of the present invention is preferably 2000 to 200000 and more preferably 4000 to 100000.

In the present invention, the number average molecular weight is a value in terms of polystyrene based on a calibration curve prepared by a gel permeation chromatography (GPC) apparatus using standard polystyrene.

By setting the number average molecular weight within the above-mentioned numerical ranges, it is possible to improve the mechanical properties as well as moldability of the molded article obtained by using this polyimide compound.

The polyimide compound of the present invention can be produced by a conventionally known method using a diamine compound represented by the above-described general formula (1) and an acid anhydride represented by the above-described general formula (2). Specifically, the polyimide compound can be obtained by reacting a diamine compound and an acid anhydride to obtain a polyamide acid, followed by a cyclodehydration reaction for conversion to a polyimide compound.

The mixing ratio of the acid anhydride and the diamine compound is preferably 0.5 mol % to 1.5 mol %, more preferably 0.9 mol % to 1.1 mol % of the total amount of the diamine compound with respect to 1 mol % of the total amount of the acid anhydride. This makes it possible to further improve the heat resistance and transparency of the polyimide compound.

The reaction between the diamine compound and the acid anhydride is preferably carried out in an organic solvent. There is no particular limitation to the organic solvents as long as they do not react with the diamine compound and the acid anhydride of the present invention and can dissolve the reaction product between the diamine compound and the acid anhydride, examples thereof being N-methyl-2-pyrrolidone, N,N-dimethylformamide, N,N-dimethylacetamide, N,N'-dimethyl imidazolidinone, γ-butyrolactone, dimethyl sulfoxide, sulfolane, 1,3-dioxolane, tetrahydrofuran, ethylene glycol monomethyl ether, ethylene glycol monoethyl ether, propylene glycol monomethyl ether, propylene glycol monoethyl ether, ethylene glycol dimethyl ether, ethylene glycol diethyl ether, ethylene glycol dibutyl ether, diethylene glycol dimethyl ether, diethylene glycol diethyl ether, diethylene glycol methyl ethyl ether, dipropylene glycol dimethyl ether, diethylene glycol dibutyl ether, dibenzyl ether, ethylene glycol monoethyl ether acetate, diethylene glycol monobutyl ether acetate, propylene glycol monomethyl ether acetate, propyl acetate, propylene glycol diacetate, butyl acetate, isobutyl acetate, 3-methoxybutyl acetate, 3-methyl-3-methoxybutyl acetate, benzyl acetate, butyl carbitol acetate, methyl lactate, ethyl lactate, butyl lactate, methyl benzoate, ethyl benzoate, triglyme, tetraglyme, acetylacetone, methyl propyl ketone, methyl butyl ketone, methyl isobutyl ketone, cyclopentanone, 2-heptanone, butyl alcohol, isobutyl alcohol, pentanol, 4-methyl-2-pentanol, 3-methyl-2-butanol, 3-methyl-3-methoxybutanol, diacetone alcohol, toluene, xylene, and the like.

From the viewpoint of solubility of the polyimide compound of the present invention, N-methyl-2-pyrrolidone, N,N'-dimethylimidazolidinone, and γ-butyrolactone are preferable in the polyimide.

The reaction temperature between the diamine compound and the acid anhydride is preferably 40° C. or lower in the case of chemical imidization. In the case of thermal imidization, the reaction temperature is preferably 150 to 220° C. and more preferably 170 to 200° C.

An imidization catalyst may be used in the cyclodehydration reaction, examples thereof being methylamine, ethylamine, trimethylamine, triethylamine, propylamine, tripropylamine, butylamine, tributylamine, tert-butylamine, hexylamine, triethanolamine, N,N-dimethylethanolamine, N,N-diethylethanolamine, triethylenediamine, N-methylpyrrolidine, N-ethylpyrrolidine, aniline, benzylamine, toluidine, trichloroaniline, pyridine, collidine, lutidine, picoline, quinoline, isoquinoline, valerolactone, and the like.

If necessary, azeotropic dehydrating agents such as toluene, xylene, and ethylcyclohexane, and acid catalysts such as acetic anhydride, propionic anhydride, butyric anhydride, and benzoic anhydride can be used.

In the reaction between a diamine compound and an acid anhydride, a sealing agent such as benzoic acid, phthalic anhydride, or hydrogenated phthalic anhydride can be used.

Furthermore, a double bond or a triple bond can be introduced into the terminal of the polyimide compound by using maleic anhydride, ethynylphthalic anhydride, methylethynylphthalic anhydride, phenylethynylphthalic anhydride, phenylethynyl trimellitic anhydride, 3- or 4-ethynylaniline, or the like.

By introducing a double bond or a triple bond into the polyimide compound, the polyimide compound of the present invention can be used as a thermosetting resin.

(Diamine Compound)

The diamine compound used in the synthesis of a polyimide compound of the present invention is characterized in that it is represented by the following general formula (1).

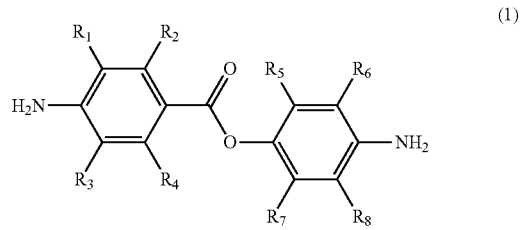

(1)

In the above formula, $R_1$ to $R_8$ are each independently selected from the group consisting of hydrogen, fluorine, substituted or unsubstituted alkyl groups and substituted or unsubstituted aromatic groups, and at least one of $R_1$ to $R_8$ is an aromatic group. Preferably, one or two of $R_1$ to $R_8$ are an aromatic group.

Preferably, one or two of $R_5$ to $R_8$ are substituted or unsubstituted aromatic groups, and more preferably at least $R_5$ or $R_7$ are aromatic groups.

By having aromatic groups in the above-mentioned positions, it is possible to suppress steric hindrance of the diamine compound, and polymerization reaction with an acid anhydride, etc. can be promoted favorably.

In a particularly preferred embodiment, one or two of $R_5$ to $R_8$ are substituted or unsubstituted aromatic groups, and $R_1$ to $R_8$ other than the aromatic group are selected from the group consisting of hydrogen, fluorine and substituted or unsubstituted alkyl groups.

Specific examples include compounds represented by the following formula (3) (an embodiment in which $R_7$ is an aromatic group and $R_1$ to $R_6$ and $R_8$ other than $R_7$ are hydrogen).

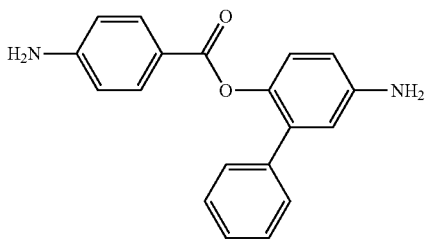

(3)

In the present invention, the alkyl group includes linear, branched and cyclic alkyl groups, and further includes an alkoxy group or an alkylamino group that bind to the main skeleton via an oxygen atom or a nitrogen atom.

Similarly, the aromatic group also includes a substituent bonded to the main skeleton via an oxygen atom, a nitrogen atom or a carbon atom. In addition, the aromatic group includes a hetero aromatic group such as a pyrrole group.

The alkyl group and the aromatic group are preferably unsubstituted from the viewpoint that the diamine compound of the present invention can be easily synthesized and utilized in the field of electronic component materials, but may have a substituent, for example, an alkyl group, halogen group such as fluoro group or chloro group, amino group, nitro group, hydroxyl group, cyano group, carboxyl group, sulfonic acid group, and the like. The alkyl group and the aromatic group may have one or more or two or more of these substituents.

The alkyl group preferably has 1 to 10 carbons and more preferably 1 to 3 carbons.

Examples of the alkyl group having 1 to 10 carbons include a methyl group, ethyl group, n-propyl group, iso-propyl group, n-butyl group, tert-butyl group, n-pentyl group, sec-pentyl group, n-hexyl group, cyclohexyl group, n-heptyl group, n-octyl group, n-nonyl group, n-decyl group, fluoromethyl group, difluoromethyl group, trifluoromethyl group, chloromethyl group, trichloromethyl group, bromomethyl group, dibromomethyl group, tribromomethyl group, fluoroethyl group, difluoroethyl group, trifluoroethyl group, chloroethyl group, dichloroethyl group, trichloroethyl group, bromoethyl group, dibromoethyl group, tribromoethyl group, hydroxymethyl group, hydroxyethyl group, hydroxylpropyl group, methoxy group, ethoxy group, n-propoxy group, n-butoxy group, n-pentyloxy group, sec-pentyloxy group, n-hexyloxy group, cyclohexyloxy group, n-heptyloxy group, n-octyloxy group, n-nonyloxy group, n-decyloxy group, trifluoromethoxy group, methylamino group, dimethylamino group, trimethylamino group, ethylamino group, propylamino group, and the like.

Among the above-mentioned alkyl groups, a methyl group, ethyl group, methoxy group, ethoxy group, and trifluoromethyl group are preferable because of steric hindrance and heat resistance.

The aromatic group preferably has 5 to 20 carbons and more preferably 6 to 10 carbons.
Examples of the aromatic group having 5 to 20 carbons include hetero aromatic groups such as a phenyl group, tolyl group, methylphenyl group, dimethylphenyl group, ethylphenyl group, diethylphenyl group, propylphenyl group, butylphenyl group, fluorophenyl group, pentafluorophenyl group, chlorophenyl group, bromophenyl group, methoxyphenyl group, dimethoxyphenyl group, ethoxyphenyl group, diethoxyphenyl group, benzyl group, methoxybenzyl group, dimethoxybenzyl group, ethoxybenzyl group, diethoxybenzyl group, aminophenyl group, aminobenzyl group, nitrophenyl group, nitrobenzyl group, cyanophenyl group, cyanobenzyl group, phenethyl group, phenylpropyl group, phenoxy group, benzyloxy group, phenylamino group, diphenylamino group, biphenyl group, naphthyl group, phenylnaphthyl group, diphenylnaphthyl group, anthryl group, anthrylphenyl group, phenylanthryl group, naphtacenyl group, phenanthryl group, phenanthrylphenyl group, phenylphenanthryl group, pyrenyl group, phenylpyrenyl group, fluorenyl group, phenylfluorenyl group, naphthylethyl group, naphthylpropyl group, anthracenyl group, phenanthryl ethyl group, and hetero aromatic groups such as pyrrole group, imidazole group, thiazole group, oxazole group, furan group, thiophene group, triazole group, pyrazole group, isoxazole group, isothiazole group, pyridine group, pyrimidine group, benzofuran group, benzothiophene group, quinoline group, isoquinoline group, indolyl group, benzothiazolyl group, carbazolyl group, and the like.

Among the above-mentioned aromatic groups, a phenyl group, phenoxy group, benzyl group, and benzyloxy group are preferable in view of availability of starting materials and cost for synthesis.

(Method for Synthesizing Diamine Compound)

The diamine compound can be obtained by reacting a compound represented by the following general formula (4) with a compound represented by the following general formula (5) and subsequently reducing a nitro group.

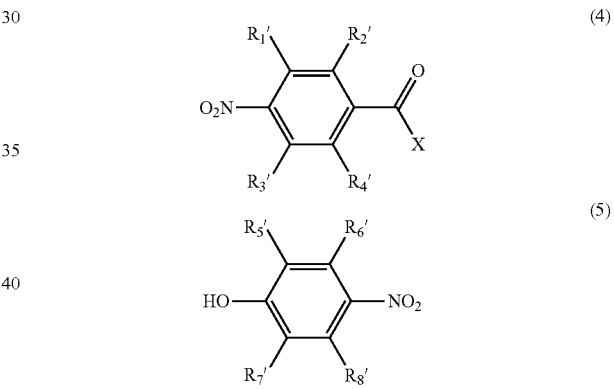

In the above formula, $R_1'$ to $R_8'$ are each independently selected from the group consisting of hydrogen, substituted or unsubstituted alkyl groups, and substituted or unsubstituted aromatic groups, and at least one of $R_1'$ to $R_8'$ is an aromatic group.

Preferably, at least one of $R_5'$ to $R_8'$ is a substituted or unsubstituted aromatic group, and more preferably at least $R_5'$ or $R_7'$ is an aromatic group.

In a particularly preferred embodiment, one of $R_5'$ to $R_8'$ is a substituted or unsubstituted aromatic group, and $R_1'$ to $R_8'$ other than an aromatic group are hydrogen.

In the above formula, X represents a hydroxyl group or a halogen group selected from a fluoro group, chloro group, bromo group, and iodo group. From the viewpoint of reactivity with the compound represented by general formula (5), X is preferably a halogen group and more preferably a chloro group or a bromo group.

In the case where X in the general formula (4) above is a hydroxyl group, the reaction of the compounds represented by the general formulae (4) and (5) above is preferably carried out in the presence of a catalyst or a dehydration condensation agent.

Examples of the catalyst include organic or inorganic basic compounds such as dimethylaminopyridine, tri-n-butylamine, pyridine, lysine, imidazole, sodium carbonate, sodium alcoholate, and potassium hydrogencarbonate, and organic or inorganic acids such as toluene sulfonate, methane sulfonate, and sulfuric acid.

Examples of the dehydration condensation agent include carbodiimides such as N,N'-dicyclohexylcarbodiimide (DCC), N,N'-diisopropylcarbodiimide, and N-cyclohexyl-N'-(4-diethylamino)cyclohexylcarbodiimide.

In Formula (4) above, when X is a halogen group, the reaction of the compounds represented by general formulae (4) and (5) above is preferably carried out in the presence of an acid acceptor. Specific examples thereof include trialkylamines such as triethylamine, tributylamine and N,N-dimethylcyclohexylamine, aliphatic cyclic tertiary amines such as N-methylmorpholine, aromatic amines such as N,N-dimethylaniline and triphenylamine, and heterocyclic amines such as pyridine, picoline, lutidine and quinoline.

More specifically, the diamine compound represented by formula (3) above can be obtained by reacting the compounds represented by the following formulae (6) and (7).

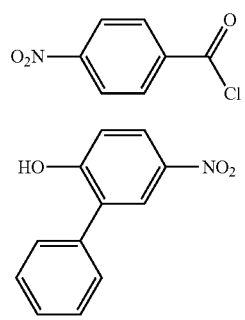

(6)

(7)

The compound represented by general formula (5) above can be obtained by nitration of a commercially available or synthesized compound represented by the following general formula (8). Nitration of the compound represented by the following general formula (8) can be carried out by a conventionally known nitration method using mixed acid of concentrated sulfuric acid and concentrated nitric acid, nitric acid, fuming nitric acid, alkali metal acid salt in concentrated sulfuric acid, acetyl nitrate, nitronium salt, nitrogen oxide, and the like.

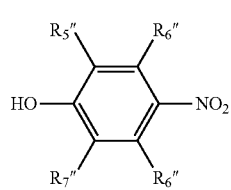

(8)

$R_5''$ to $R_8''$ are each independently selected from the group consisting of hydrogen, substituted or unsubstituted alkyl groups, and substituted or unsubstituted aromatic groups. Preferably, at least one or preferably a one or two of $R_5''$ to $R_8''$ are aromatic groups.

The content of the diamine compound represented by general formula (1) in the polyimide compound is preferably 5 mol % to 50 mol % and more preferably 10 mol % to 40 mol %. Accordingly, the heat resistance and transparency of the polyimide compound can be further improved.

(Alicyclic Tetracarboxylic Acid Dianhydride)

The alicyclic tetracarboxylic acid dianhydride used in the synthesis of the polyimide compound of the present invention is characterized in that it is represented by the following general formula (2).

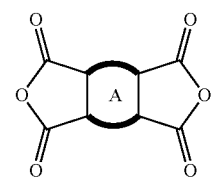

(2)

In the above formula, A represents an alicyclic structure. Examples of the alicyclic structure include the following structures.

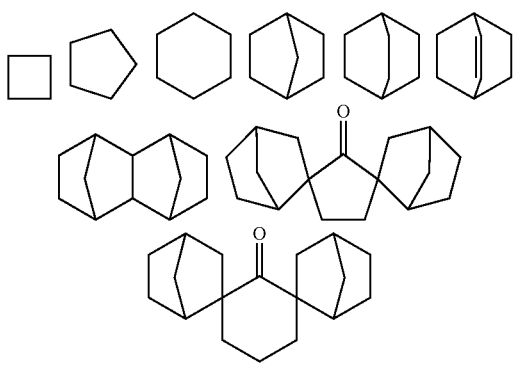

Specific examples of the alicyclic tetracarboxylic acid dianhydride include the following compounds. The polyimide compound may contain two or more alicyclic tetracarboxylic acid dianhydride compounds. In addition, the compounds described below may have a substituent, for example, a halogen group such as an alkyl group, fluoro group or chloro group, an amino group, nitro group, hydroxyl group, cyano group, carboxyl group, sulfonic acid group, and the like. Among these, an alkyl group is preferable, and an alkyl group having 1 to 4 carbons is more preferable.

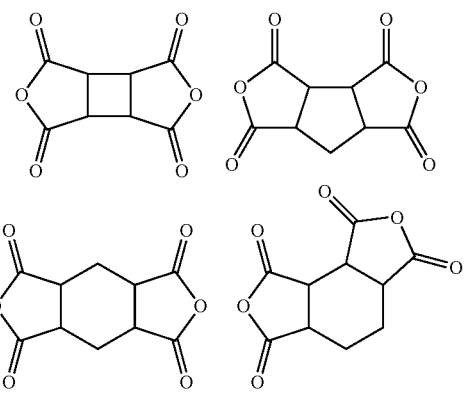

-continued

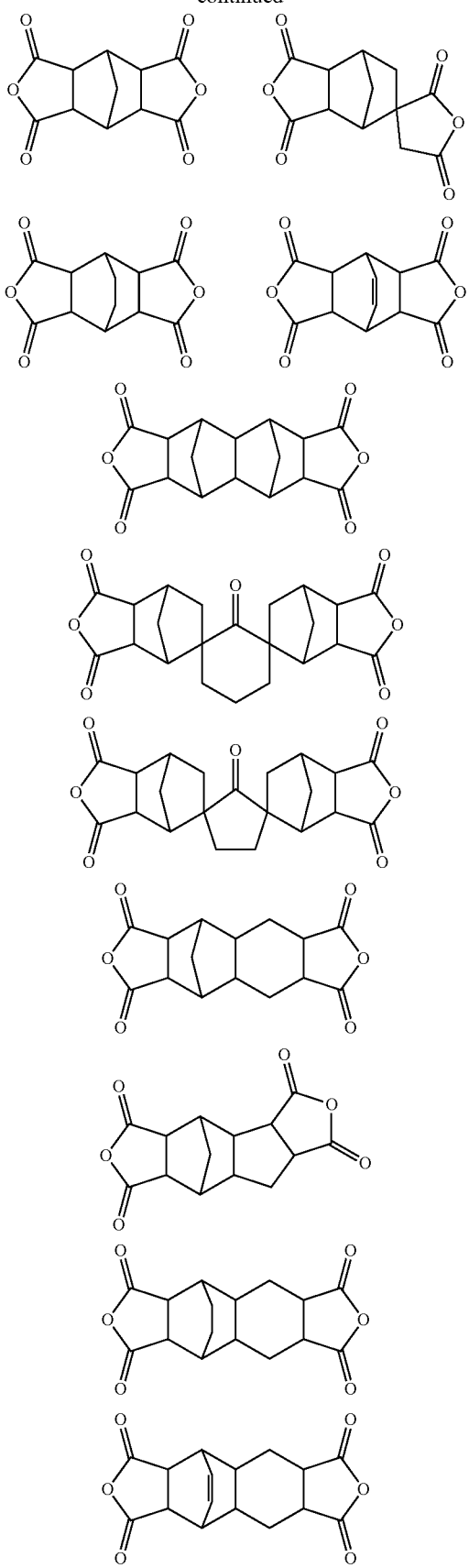

Among the tetracarboxylic acid dianhydrides described above, the following compounds are preferable from the viewpoint of heat resistance and transparency of the polyimide compound.

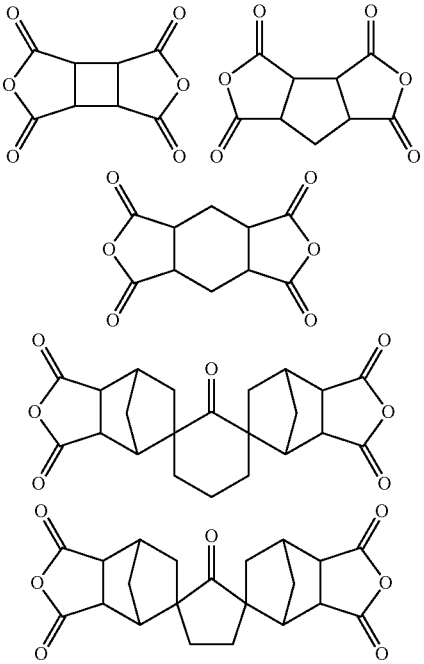

The content of the alicyclic tetracarboxylic acid dianhydride represented by general formula (2) in the polyimide compound is preferably 10 mol % to 60 mol % and more preferably 20 mol % to 50 mol %. This enables to further improve heat resistance and transparency of the polyimide compound.

(Fluorene Compound)

In one embodiment, the polyimide compound can include a fluorene compound as a polymerization component. This makes it possible to reduce the phase difference of the polyimide compound while maintaining its heat resistance.

In the present invention, the fluorene compound may be a diamine compound having a fluorene structure or an acid anhydride having a fluorene structure.

Examples of the diamine compound having a fluorene structure include the following compounds.

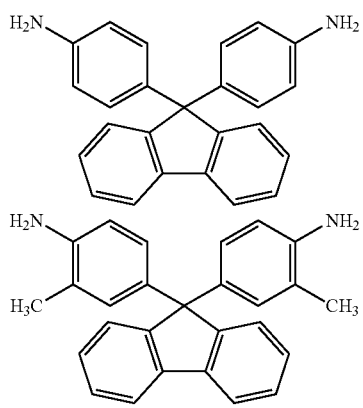

-continued

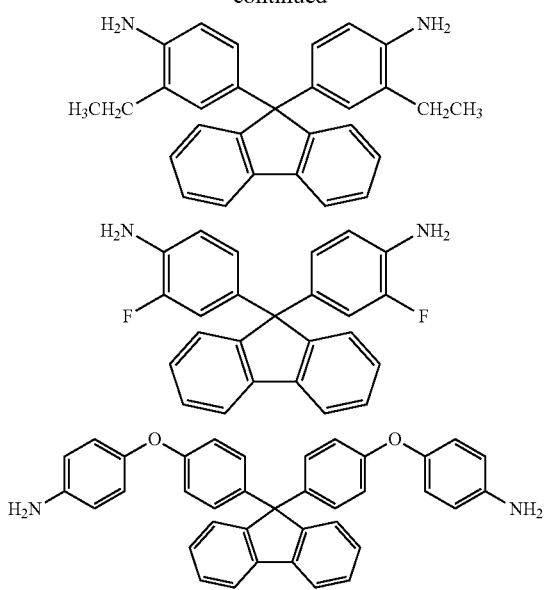

Examples of the acid anhydride having a fluorene structure include the following compounds.

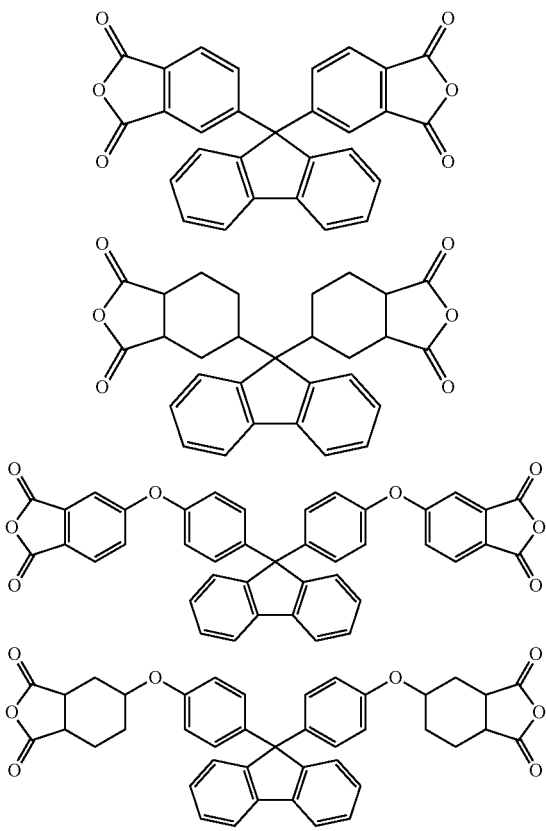

The content of the fluorene compound in the polyimide compound is preferably 5 mol % to 60 mol % and more preferably 15 mol % to 50 mol %. This makes it possible to further reduce the phase difference while maintaining the heat resistance of the polyimide compound.

(Another Diamine Compound)

The polyimide compound of the present invention may contain, as a polymerization component, a diamine compound other than the diamine compound represented by the above general formula (1) (hereinafter referred to as another diamine compound). Another diamine compound includes, for example, 2,2'-bis(trifluoromethyl)benzidine, m-phenylenediamine, p-phenylenediamine, 2,4-diaminotoluene, 2,4(6)-diamino-3,5-diethyltoluene, 5(6)-amino-1,3,3-trimethyl-1-(4-aminophenyl)indane, 4,4'-diamino-2,2'-dimethyl-1,1'-biphenyl, 4,4'-diamino-3,3'-dimethyl-1, 1'-biphenyl, 3,4'-diaminodiphenylether, 4,4'-diaminodiphenylether, 3,3'-diaminodiphenylsulfone, 4,4'-diaminodiphenylsulfone, 4,4'-diaminodiphenylsulfide, 4-aminophenyl-4-aminobenzoate, 4,4'-(9-fluorenylidene)cyaniline, 9,9'-bis(3-methyl-4-aminophenyl)fluorene, 1,3-bis(3-aminophenoxy)benzene, 1,3-bis(4-aminophenoxy)benzene, 1,4-bis(4-aminophenoxy)benzene, 2,2-bis(4-aminophenyl)propane, 2,2-bis(3-methyl-4-aminophenyl)propane, 4,4'-(hexafluoroisopropylidene)dianiline, 2,2-bis(3-amino-4-methylphenyl)hexafluoropropane, 2,2-bis[4-(4-aminophenoxy)phenyl]propane, 2,2-bis[4-(4-aminophenoxy)phenyl]hexafluoropropane, α,α-bis[4-(4-aminophenoxy)phenyl]-1,3-diisopropylbenzene, α,α-bis[4-(4-aminophenoxy)phenyl]-1,4-diisopropylbenzene, 3,7-diamino-dimethyldibenzothiophene 5,5-dioxide, bis(3-carboxy-4-aminophenyl)methylene, 3,3'-diamino-4,4'-dihydroxy-1,1'-biphenyl, 4,4'-diamino-3,3'-dihydroxy-1,1'-biphenyl, 2,2-bis(3-amino-4-hydroxyphenyl)propane, 2,2-bis(3-hydroxy-4-hydroxyphenyl)hexafluoropropane, 1,3-bis(3-hydroxy-4-aminophenoxy)benzene, 2,2-bis(3-hydroxy-4-aminophenyl) benzene, 3,3'-diamino-4,4'-dihydroxydiphenylsulfone, and the like.

Preferred among the above described are 2,2'-bis(trifluoromethyl)benzidine, 5(6)-amino-1,3,3-trimethyl-1-(4-aminophenyl)-indane3,3'-diaminodiphenylsulfone, and 4,4'-diaminodiphenylsulfone.

When the diamine compound having a benzidine skeleton is contained in the polyimide compound as a polymerizable component, the thermal expansion coefficient can be lowered, and when the diamine compound having an indane skeleton and a sulfone group is contained, transparency can be increased.

The content of another diamine compound in the polyimide compound of the present invention is preferably 5 mol % to 70 mol % and more preferably 15 mol % to 60 mol %. This enables to obtain a transparent polyimide having excellent heat resistance.

(Another Acid Anhydride)

The polyimide compound of the present invention may contain, as a polymerization component, an acid anhydride other than the acid anhydride represented by general formula (2) above (hereinafter referred to as another acid anhydride). Examples of another acid anhydride include oxydiphthalic acid, pyromellitic acid dianhydride, 3-fluoropyromellitic acid dianhydride, 3,6-difluoropyromellitic acid dianhydride, 3,6-bis(trifluoromethyl)pyromellitic acid dianhydride, 1,2,3,4-benzenetetracarboxylic acid dianhydride, 2,2',3,3'-benzophenone tetracarboxylic acid dianhydride, 3,3',4,4'-benzophenone tetracarboxylic acid dianhydride, 3,3',4,4'-biphenyltetracarboxylic acid dianhydride, 3,3',4,4'-biphenylsulphonetetracarboxylic acid dianhydride, 4,4'-(4,4'-isopyridenediphenoxy)bisphthalic acid dianhydride, 1,2,4,5-cyclohexanetetracarboxylic acid dianhydride, 2,3,3',4'-biphenyl tetracarboxylic acid dianhydride, 3,3'',4,4''-terphenyl tetracarboxylic acid dianhydride, 3,3''',4,4'''-quarterphenyl tetracarboxylic acid dianhydride, 2,2',3,3'-biphenyl tetracarboxylic acid dianhydride, methylene-4,4'- diphthalic acid dianhydride, 1,1-ethenylidene-4,4'diphthalic acid dianhydride, 2,2-propylidene-4,4'-diphthalic acid dianhydride, 1,2-ethylene-4,4'-diphthalic acid dianhydride, 1,3-trimethylene-4,4'-diphthalic acid dianhydride, 1,4-tetramethylene-4,4'-diphthalic acid dianhydride, 1,5-pentamethylene-4,4'-diphthalic acid dianhydride, 1,3-bis[2-(3,4-dicarboxyphenyl)-2-propyl]benzene dianhydride, 1,4-bis[2-(3,4-dicarboxyphenyl)-2-propyl]benzene dianhydride, bis[3-(3,4-dicarboxyphenoxy)phenyl]methane dianhydride, bis[4-(3,4-dicarboxyphenoxy)phenyl]methane dianhydride, 2,2-bis[3-(3,4-dicarboxyphenoxy)phenyl]propane dianhydride, 2,2-bis[4-(3,4-dicarboxyphenoxy)phenyl]propane dianhydride, difluoromethylene-4,4'-diphthalic acid dianhydride, 1,1,2,2-tetrafluoro-1,2-ethylene-4,4'-diphthalic acid dianhydride, 3,3',4,4'-diphenylsulfonic tetracarboxylic acid dianhydride, oxy-4,4'-diphthalic acid dianhydride, bis(3,4-dicarboxyphenyl)ether dianhydride, thio-4,4'-diphthalic acid dianhydride, sulfonyl-4,4'-diphthalic acid dianhydride, 1,3-bis(3,4-dicarboxyphenyl)benzene dianhydride, 1,4-bis(3,4-dicarboxyphenoxy)benzene dianhydride, 1,3-bis(3,4-dicarboxyphenoxy)benzene dianhydride, 1,4-bis(3,4-dicarboxyphenoxy)benzene dianhydride, bis(3,4-dicarboxyphenoxy)dimethyl silane dianhydride, 1,3-bis(3,4-dicarboxyphenoxy)-1,1,3,3-tetramethyl disiloxane dianhydride, 2,3,6,7-naphthalene tetracarboxylic acid dianhydride, 1,2,5,6-naphthalene tetracarboxylic acid dianhydride, 3,4,9,10-perylenetetracarboxylic acid dianhydride, 2,3,6,7-antracene tetracarboxylic acid dianhydride, 1,2,7,8-phenanthrene tetracarboxylic acid dianhydride, 1,2,3,4-butene tetracarboxylic acid dianhydride, 3,3',4,4'-bicyclohexyl tetracarboxylic acid dianhydride, carbonyl-4,4'-bis(cyclohexane-1,2-dicarboxylic acid) dianhydride, methylene-4,4'-bis(cyclohexane-1,2-dicarboxylic acid) dianhydride, 1,2-ethylene-4,4'-bis(cyclohexane-1,2-dicarboxylic acid)dianhydride, oxy-4,4'-bis(cyclohexane-1,2-dicarboxylic acid) dianhydride, thio-4,4'-bis(cyclohexane-1,2-dicarboxylic acid) dianhydride, sulfonyl-4,4'-bis(cyclohexane-1,2-dicarboxylic acid) dianhydride, 3,3',5,5'-tetrakis(trifluoromethyl)oxy-4,4'-diphthalic acid dianhydride, 3,3',6,6'-tetrakis(trifluoromethyl)oxy-4,4'-diphthalic acid dianhydride, 5,5',6,6'-tetrakis(trifluoromethyl)oxy-4,4'-diphthalic acid dianhydride, 3,3',5,5',6,6'-hexakis(trifluoromethyl)oxy-4,4'-diphthalic acid dianhydride, 3,3'-difluorosulfonyl-4,4'-diphthalic acid dianhydride, 5,5'-difluorosulfonyl-4,4'-diphthalic acid dianhydride, 6,6'-difluorosulfonyl-4,4'-diphthalic acid dianhydride, 3,3',5,5',6,6'-hexafluorosulfonyl-4,4'-diphthalic acid dianhydride, 3,3'-bis(trifluoromethyl)sulfonyl-4,4'-diphthalic acid dianhydride, 5,5'-bis(trifluoromethyl)sulfonyl-4,4'-diphthalic acid dianhydride, 6,6'-bis(trifluoromethyl)sulfonyl-4,4'-diphthalic acid dianhydride, 3,3',5,5'-tetrakis(trifluoromethyl)sulfonyl-4,4'-diphthalic acid dianhydride, 3,3',6,6'-tetrakis(trifluoromethyl)sulfonyl-4,4'-diphthalic acid dianhydride, 5,5',6,6'-tetrakis(trifluoromethyl)sulfonyl-4,4'-diphthalic acid dianhydride, 3,3',5,5',6,6'-hexakis(trifluoromethyl)sulfonyl-4,4'-diphthalate dianhydride, 3,3'-difluoro-2,2-perfluoropropylidene-4,4'-diphthalic acid dianhydride, 5,5'-difluoro-2,2-perfluoropropylidene-4,4'-diphthalic acid dianhydride, 6,6'-difluoro-2,2-perfluoropropylidene-4,4'-diphthalic acid dianhydride, 3,3',5,5',6,6'-hexafluoro-2,2-perfluoropropylidene-4,4'-diphthalic acid dianhydride, 3,3'-bis(trifluoromethyl)-2,2-perfluoropropylidene-4,4'-diphthalic acid dianhydride, ethylene glycol bistrimellitate dianhydride, and the like.

The content of another acid anhydride in the polyimide compound of the present invention is preferably 30 mol % or less and more preferably 25 mol % or less. This enables to obtain a transparent polyimide having excellent film properties and heat resistance.

(Purpose)

The polyimide compound of the present invention can be used, for example, electronic material parts such as a housing, a flexible printed circuit board, and a printed wiring board used in a personal computer, a cellular phone, or the like; parts for an image display device such as an organic EL display device; parts for a touch panel; and parts for a solar cell panel such as a surface protection layer and a substrate.

(Molded Article)

A molded article of the present invention is characterized by containing the above-described polyimide compound.

The shape of the molded article according to the present invention is not particularly limited, and may be appropriately changed in accordance with the purpose thereof. For example, it may be in the form of a film or a sheet.

The content of the polyimide compound in the molded article of the present invention is preferably 30 mass % to 100 mass %, more preferably 50 mass % to 100 mass %, and further preferably 60 mass % to 100 mass %.

The molded article of the present invention may contain another compound as long as the properties thereof are not impaired, examples including a polyolefin-based resin, polyester-based resin, cellulose-based resin, vinyl-based resin, polycarbonate-based resin, polyamide-based resin, styrene-based resin, ionomer-based resin, and the like.

In addition, the molded article of the present invention may contain various additives as long as the properties thereof are not impaired. Examples of the additives include a plasticizer, ultraviolet stabilizer, coloring inhibitor, matting agent, deodorant, flame retardant, weathering agent, antistatic agent, thread friction reducing agent, slip agent, demolding agent, antioxidant, ion exchanger, dispersant, ultraviolet absorber, and colorants such as pigment and dye.

The total light transmittance of the molded article of the present invention is preferably 85% or more and more preferably 90% or more.

In the present invention, the total light transmittance of the molded article can be measured according to JIS K 7136, 7375.

The molded article of the present invention preferably has a coefficient of thermal expansion (CTE) of 35 ppm/K or less, more preferably 30 ppm/K or less, and further preferably 25 ppm/K or less.

In the present invention, the coefficient of thermal expansion (CTE) of the molded article refers to an average coefficient of thermal expansion (CTE) from 100° C. to 250° C. when the molded article is heated from room temperature to 450° C. at a heating temperature of 10° C./min under a load of 5 g using TMA-60 (product name) manufactured by Shimadzu Corporation.

The 5% weight loss temperature of the molded article of the present invention is preferably 420° C. or higher and more preferably 450° C. or higher.

In the present invention, the 5% weight loss temperature of the molded article can be measured in accordance with JIS K 7120 using a thermomechanical analyzer (for example, product name: TGA-50 manufactured by Shimadzu Corporation) at a temperature rising rate of 5° C./min in nitrogen.

The glass transition temperature (Tg) of the molded article of the present invention is preferably 280° C. or higher, more preferably 300° C. or higher, and further preferably 340° C. or higher.

In the present invention, the glass transition temperature (Tg) of the molded article can be measured in accordance with JIS K 7121 using a thermomechanical analyzer (product name: DSC-60 Plus, manufactured by Shimadzu Corporation) under a nitrogen flow at a heating rate of 10° C./min.

(Method for Producing Molded Article)

In one embodiment, the molded article of the present invention can be produced by dissolving the polyimide compound described above in the organic solvent such as N-methyl-2-pyrrolidone (NMP), coating the polyimide compound on a substrate such as a copper foil, and drying the coating. This can give a film-like molded article.

Depending on the purpose, the substrate may be removed by peeling the substrate from the molded article or performing etching treatment.

A molded article using the polyimide compound of the present invention can be produced only by a step of applying a polyisoimide compound or a polyimide compound on the substrate and drying, and it is possible to omit the step of high-temperature heat-drying accompanied by an imidization reaction carried out by a conventional method. In addition, since the heat-drying step can be omitted, heat resistance of the substrate need not be taken into consideration, and the molded article of the present invention can be produced on various substrates.

The molded article of the present invention can also be produced by conventionally known methods such as press molding, transfer molding, injection molding, and the like.

EXAMPLES

Example 1

Synthesis of Diamine Compound

To a 1 L 4-neck flask equipped with a thermometer and a stirrer, 500 g of toluene and 51.06 g (0.30 mol) of commercially available o-phenylphenol (manufactured by Wako Pure Chemical Industries, Ltd.) were added and 30 g (0.33 mol) of 70 wt % nitric acid (d=1.42) was added dropwise over 2 hours while cooling to keep the reaction temperature at −5 to 0° C. Further, the reaction was finished by stirring at the same temperature for 3 hours.

The product slurry was collected by filtration and washed with aqueous sodium hydrogen carbonate and then with water. Then, the mixture was dried under reduced pressure to obtain light yellow to yellow 2-hydroxy-5-aminobiphenyl represented by the following formula (A).

The purity by HPLC analysis (area %) was 97.01%, and the melting point by DSC measurement was 128° C. (endothermic peak). $^1$H-NMR (CDCl3) σ 5.84 ppm (1H for OH of phenol), σ 6.99 ppm (1H for o-position of phenol), σ 7.15 to 7.50 ppm (5H for o-phenyl), σ 8.12 to 8.20 ppm (2H for m-position of phenol) confirmed the introduction of a nitro group at p-position of phenol.

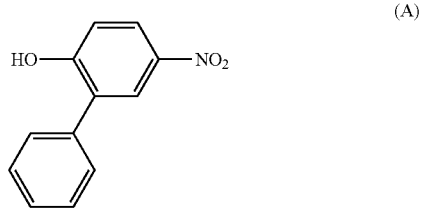 [SMILES: O=[N+]([O-])c1ccc(O)c(-c2ccccc2)c1]

(A)

To a 1 L 4-neck flask equipped with a thermometer, a stirrer, and a reflux cooling tube, 43.04 g (0.20 mol) of 2-hydroxy-5-nitrobiphenyl synthesized as described above, 45.53 g (0.24 mol) of commercially available 4-nitrobenzoyl chloride represented by the following formula (B), and 500 g of N,N'-dimethylformamide were added, and the mixture was stirred at about 15° C.

Then, 30.36 g (0.30 mol) of triethylamine was slowly added. After the addition was completed, the reaction was continued for 3 hours while heating at 50° C. After the reaction was completed, the mixture was cooled to 25° C. and ion-exchanged water was added to obtain a precipitate. After the temperature reached 25° C., the precipitate was collected by filtration, washed several times with methanol and ion-exchanged water, and dried under reduced pressure to obtain a compound represented by the following formula (C).

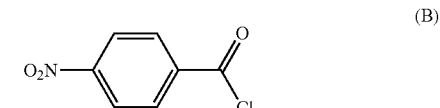

(B)

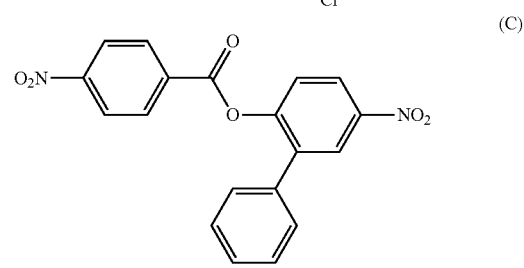

(C)

To a 500 cc autoclave equipped with a thermometer and a stirrer, 22 g (0.06 mol) of a compound represented by the above chemical formula (C), 150 ml of dimethylacetamide and 5% Pd-carbon (as a dried product) were added, and after nitrogen substitution, hydrogen substitution was performed.

When reduction was performed while keeping a hydrogen pressure of 9 kg/cm$^2$ (gauge pressure) and a temperature of 80° C., absorption of hydrogen stopped in about 2 hours. After further aging at 80° C. for 1 hour, the product solution was cooled to room temperature. After nitrogen substitution, the product solution was taken out and the catalyst was removed by filtration. The filtrate was poured into 50% methanol to precipitate crystals, and the crystals were collected.

The crystals were dried under vacuum at 50° C. to obtain a diamine compound represented by the following chemical formula (D) satisfying general formula (1). Purity by HPLC analysis (area %) was 99.04%, and the melting point by DSC measurement was 154° C. (endothermic peak).

Figure 2:
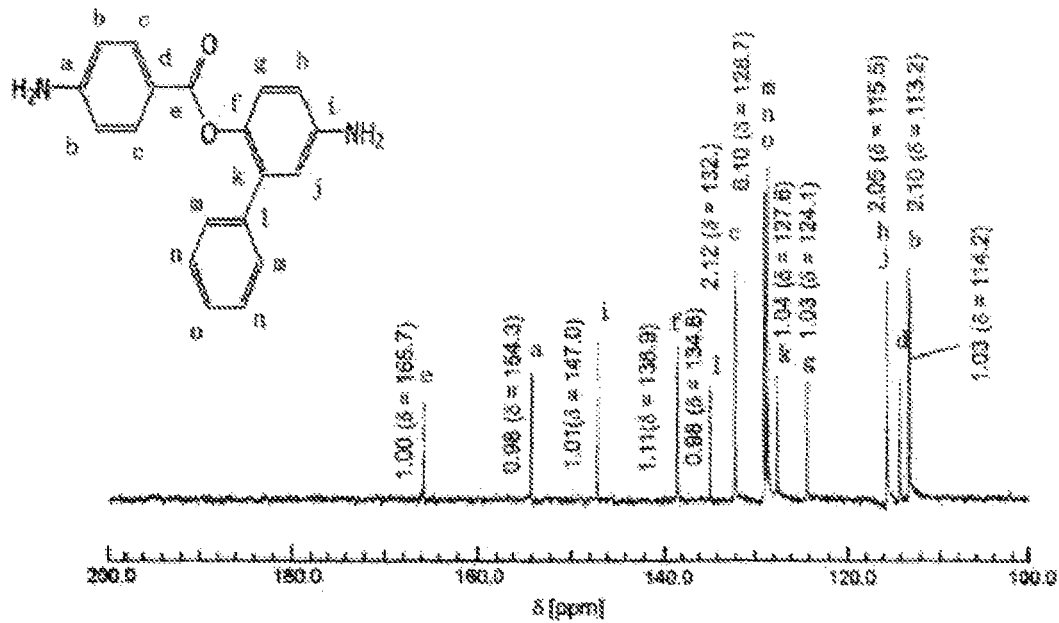
FIG. 2 shows a $^{13}$C-NMR chart of a compound represented by formula (D) obtained according to the Examples.
Figure 3:
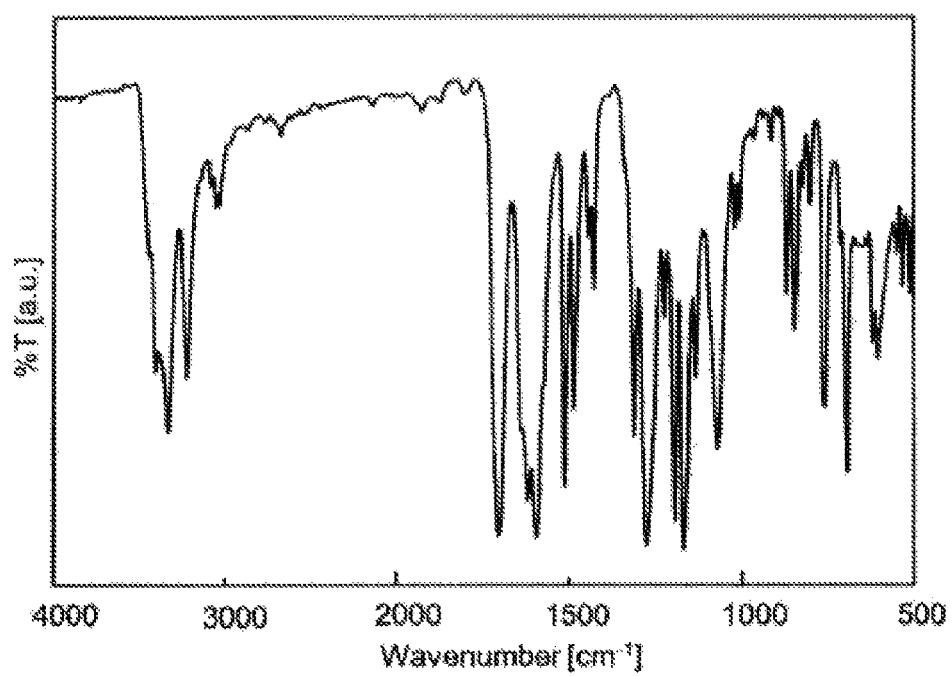
FIG. 3 shows a FT-IR chart of a compound represented by formula (D) obtained according to the Examples.

The compound was identified by $^1$H-NMR, $^{13}$C-NMR, FT-IR, and elemental analysis, and its structure was confirmed to be a compound represented by chemical formula (D). FIGS. 1 to 3 show the results of $^1$H-NMR (300 MHz, measuring instrument: Varian 300-MR spectrometer, heavy solvent: DMSO-d$_6$), $^{13}$C-NMR (75 MHz, measuring instrument: Varian 300-MR spectrometer, heavy solvent: DMSO-d$_6$), and FT-IR (KBr method, measuring instrument: FTIR-410 spectrometer).

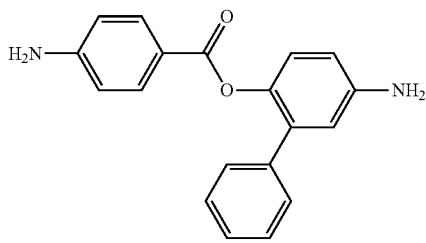

(D)

Synthesis of Polyimide Compound

Into a 500 ml separable flask equipped with a nitrogen-introducing tube and a stirring device were added 12.17 g (40 mmol) of a diamine compound (PHBAAB) represented by chemical formula (D) obtained as above, 11.77 g (60 mmol) of 1,2,3,4-cyclobutanetetracarboxylic acid dianhydride (CBDA) represented by the following chemical formula (E), 12.41 g (40 mmol) of bis(3,4-dicarboxyphenyl) ether dianhydride (ODPA) represented by the following chemical formula (F), 19.21 g (60 mmol) of 2,2'-bis(trifluoromethyl)benzidine (TFMB) represented by the following chemical formula (G), 208 g of N-methyl-2-pyrrolidone (NMP), 1.58 g of pyridine (20 mmol), and 20 g of toluene, and reaction was conducted under a nitrogen atmosphere at 180° C. while taking out toluene out from the system halfway, and 87 g of NMP was added at the end of the reaction to obtain a solution in which 15 wt % of the polyimide compound was dissolved.

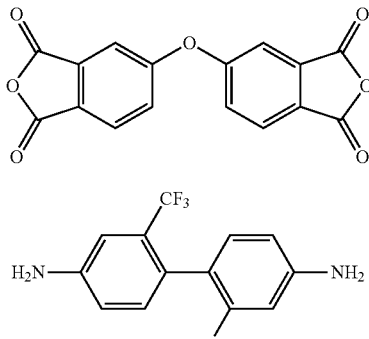

(E)

(F)

(G)

Example 2

Synthesis of Polyimide Compound

15% by weight of a polyimide solution was obtained as like Example 1 and adding 105 g of GBL after obtaining 20% by weight of a polyimide solution, except that 23.06 g (60 mmol) of octahydro-3H,3"H-dispiro[4,7-methanoisobenzofuran-5,1'-cyclo pentane-3',5" [4,7]methanoisobenzofuran]-1,1",2',3,3"(4H,4"H)-pentaone (CpODA) represented by the following chemical formula (H) was used instead of CBDA represented by chemical formula (E), and 253 g of γ-butyrolactone (GBL) was used instead of NMP.

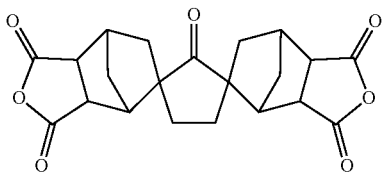

(H)

Example 3

Synthesis of Polyimide Compound

15% by weight of a polyimide solution was obtained as like Example 1 and adding 105 g of GBL after obtaining 20% by weight of a polyimide solution, except that 23.06 g (60 mmol) of CpODA represented by chemical formula (H) was used in place of CBDA represented by chemical formula (E), 18.34 g (40 mmol) of 9,9-bis(3,4-dicarboxyphenyl)fluorene dianhydride (BPAF) represented by the following chemical formula (I) was used in place of ODPA represented by chemical formula (F), and 277 g of γ-butyrolactone (GBL) was used in place of N-methyl-2-pyrrolidone (NMP).

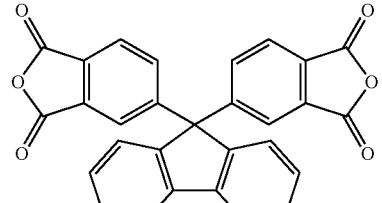

(I)

Comparative Example 1

To a 500 ml separable flask equipped with a nitrogen-introducing tube and a stirring device were introduced, 38.44 g (100 mmol) of CpODA, 32.02 g (100 mmol) of TFMB, 208 g of NMP, 1.58 g (20 mmol) of pyridine, and 20 g of toluene, and the reaction was carried out at 180° C. under a nitrogen-containing atmosphere while excluding toluene from the system halfway, and 87 g of NMP was charged at the end of the reaction to obtain a solution in which 20% by weight of a polyimide compound was dissolved.

Comparative Example 2

To a 500 ml separable flask equipped with a nitrogen-introducing tube and a stirring device were introduced, 31.02 g (100 mmol) of ODPA, 32.02 g (100 mmol) of TFMB, 208 g of NMP, 1.58 g (20 mmol) mmol) of pyridine, and 20 g of toluene, and the reaction was carried out under a nitrogen atmosphere at 180° C. while excluding toluene from the system halfway, and 87 g of NMP was introduced at the end of the reaction to obtain a solution in which 20% by weight of a polyimide compound was dissolved.

<<Performance Evaluation>>

The solutions obtained in the above Examples and Comparative Examples were coated on a glass plate by a spin coating method and dried at 100° C. for 0.5 hours, at 200° C. for 0.5 hours, and at 250° C. for 1 hour. Then, the solutions were separated from the glass plate to obtain film-form molded articles each having a thickness of about 15 μm.

Specifically, a polyimide containing only an alicyclic tetracarboxylic acid dianhydride and no PHBAAB in the diamine component as in Comparative Example 1 was not only incapable of giving a firm film but also a transparent polyimide. In the case of a polyimide free of an alicyclic tetracarboxylic acid dianhydride and PHBAAB as in Comparative Example 2, transparency is deteriorated.

TABLE 1

|  | Composition of Polyimide Compound (mol %) | | | | | | Total Light Transmittance (%) | Phase Difference (nm) | Coefficient of thermal expansion (ppm/K) | 5% Weight Loss Temperature | Glass Transition Temperature (Tg) |
| --- | --- | --- | --- | --- | --- | --- | --- | --- | --- | --- | --- |
|  | CBDA | CpODA | ODPA | BPAF | PHBAAB | TFMB | | | | | |
| Ex.1 | 30 |  | 20 |  | 20 | 30 | 90.0 | 394 | 30 | 447 | 282 |
| Ex.2 |  | 30 | 20 |  | 20 | 30 | 90.5 | 474 | 30 | 489 | 305 |
| Ex.3 |  | 30 |  | 20 | 20 | 30 | 90.2 | 373 | 17 | 490 | 344 |
| Comp. Ex.1 | 50 |  |  |  |  | 50 | Opaque | Opaque | un-measurable | 489 | un-measurable |
| Comp. Ex.2 |  |  | 50 |  |  | 50 | 88.7 | 398 | 28 | 564 | 312 |

<Total Light Transmittance>

The molded articles produced as described above were each made into a test piece having a size of 100 mm in length×100 mm in width, and the total light transmittance was measured using NDH5000 manufactured by Nippon Denshoku Industries Co., Ltd. in accordance with JIS K 7136 and 7375. The measurement results are summarized in Table 1.

<Phase Difference>

The molded articles produced as described above were each made into a test piece having a size of 100 mm in length×100 mm in width, and the phase difference was measured using an ellipsometer M-2000V-Te manufactured by J. A. Woollam. The measurement results are summarized in Table 1.

<Coefficient of Thermal Expansion (CTE)>

Using TMA-60 (product name) manufactured by Shimadzu Corporation, the test pieces above were heated from room temperature to 450° C. at a heating temperature of 10° C./min while applying a weight of 5 g, to obtain an average coefficient of thermal expansion (CTE) from 100° C. to 250° C. The results are shown in Table 1.

<5% Weight Loss Temperature>

Using TGA-50 (product name) manufactured by Shimadzu Corporation in accordance with JIS K 7120, 5% weight loss temperatures of the test pieces were measured at a heating rate of 10° C./min in air. The measurement results are shown in Table 1.

<Glass Transition Temperature (Tg)>

According to JIS K 7121, using DSC-60Plus (product name) and TMA-60 (product name) manufactured by Shimadzu Corporation, the glass transition temperatures (Tg) of the test pieces were measured under a nitrogen flow at a heating rate of 10° C./min. The measurement results are shown in Table 1.

As is clear from Table 1, it was found that a polyimide compound which is a reaction product of a diamine compound satisfying the above described general formula (1) and an alicyclic tetracarboxylic acid dianhydride satisfying the above-described general formula (2) has high transparency and heat resistance.

The invention claimed is:

1. A polyimide compound that is a reaction product of a diamine compound represented by the following general formula (1):

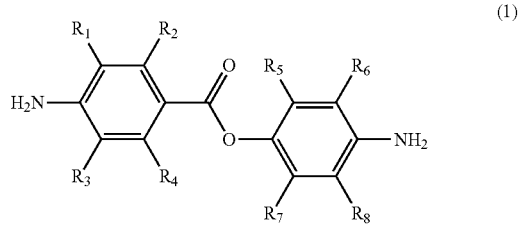

(1)

wherein $R_1$ to $R_8$ are each independently selected from the group consisting of hydrogen, fluorine, substituted or unsubstituted alkyl groups and substituted or unsubstituted aromatic groups, and at least one of $R_1$ to $R_8$ is a substituted or unsubstituted aromatic group, and an alicyclic tetracarboxylic acid dianhydride represented by the following general formula (2):

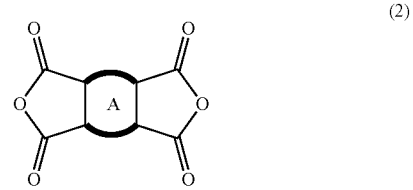

(2)

wherein

A represents an alicyclic structure selected from the group consisting of:

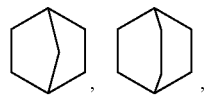

,

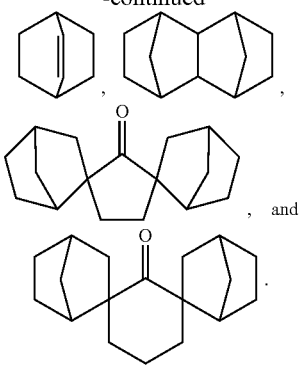

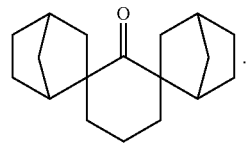

2. The polyimide compound according to claim 1, wherein
   a content of the diamine compound represented by general formula (1) in the polyimide compound is 5 mol % to 50 mol %.
3. The polyimide compound according to claim 1, wherein
   a content of the alicyclic tetracarboxylic acid dianhydride represented by general formula (2) in the polyimide compound is 10 mol % to 60 mol %.
4. The polyimide compound according to claim 1, wherein
   one or two of $R_5$ to $R_8$ are substituted or unsubstituted aromatic groups.
5. The polyimide compound according to claim 1, wherein
   one or two of $R_5$ to $R_8$ are substituted or unsubstituted aromatic groups, and $R_1$ to $R_8$ other than aromatic groups are selected from the group consisting of hydrogen, fluorine and substituted or unsubstituted alkyl groups.
6. The polyimide compound according to claim 1, wherein
   the substituted or unsubstituted aromatic group is selected from the group consisting of a phenyl group, methylphenyl group, phenoxy group, benzyl group and benzyloxy group.
7. The polyimide compound according to claim 1, further comprising a fluorene compound as a polymerization component.
8. The polyimide compound according to claim 7, wherein
   the fluorene compound is selected from the group consisting of:

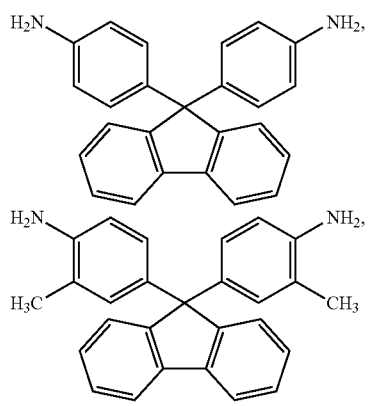

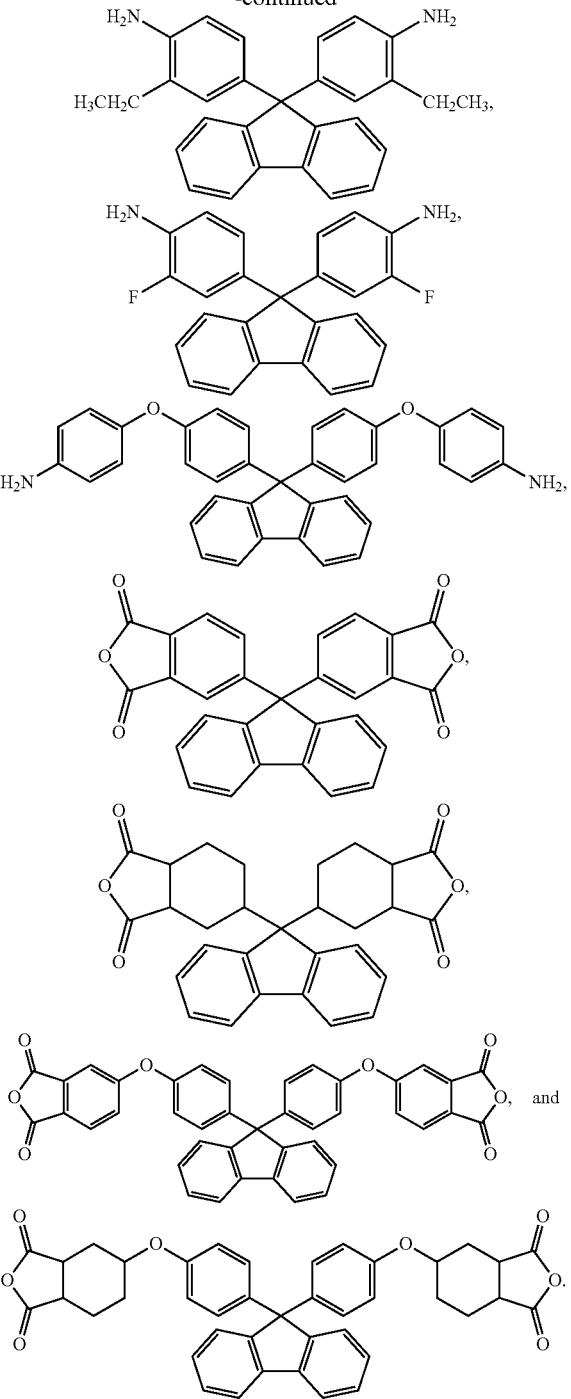

9. The polyimide compound according to claim 7, wherein
   a content of the fluorene compound in the polyimide compound is 5 mol % to 60 mol %.
10. A molded article comprising the polyimide compound according to claim 1.
11. The molded article according to claim 10, wherein the total light transmittance is 85% or more.
12. The molded article according to claim 10, wherein the coefficient of thermal expansion (CTE) is 35 ppm/K or less.

13. The molded article according to claim 10, wherein the 5% weight loss temperature is 420° C. or higher.

14. The molded article according to claim 10, wherein the glass transition temperature is 280° C. or higher.

* * * * *